US010235490B1

(12) United States Patent
Mallon et al.

(10) Patent No.: US 10,235,490 B1
(45) Date of Patent: Mar. 19, 2019

(54) METHODS AND SYSTEMS FOR CENTERING OF PINS DURING INSTANCE ABUTMENT

(71) Applicant: CADENCE DESIGN SYSTEMS, INC., San Jose, CA (US)

(72) Inventors: David Mallon, Scotland (GB); Gilles S. C. Lamant, Sunnyvale, CA (US); Kenneth Ferguson, Scotland (GB); Monika Bijoy, West Lothian (GB)

(73) Assignee: Cadence Design Systems, Inc., San Jose, CA (US)

( * ) Notice: Subject to any disclaimer, the term of this patent is extended or adjusted under 35 U.S.C. 154(b) by 38 days.

(21) Appl. No.: 15/589,731

(22) Filed: May 8, 2017

(51) Int. Cl.
*G06F 17/50* (2006.01)
*G06F 19/00* (2018.01)

(52) U.S. Cl.
CPC ...... *G06F 17/5077* (2013.01); *G06F 17/5072* (2013.01); *G06F 17/5045* (2013.01); *G06F 17/5068* (2013.01); *G06F 17/5081* (2013.01); *G06F 19/00* (2013.01)

(58) Field of Classification Search
CPC ............. G06F 17/5045; G06F 17/5068; G06F 17/5081; G06F 19/00; G06F 17/00; G06F 17/5077; G06F 17/5072
See application file for complete search history.

(56) References Cited

U.S. PATENT DOCUMENTS

| | | | | |
|---|---|---|---|---|
| 5,452,239 A * | 9/1995 | Dai | ...... | G06F 17/5027 703/19 |
| 5,461,576 A * | 10/1995 | Tsay | ...... | G06F 17/505 716/113 |
| 5,483,461 A * | 1/1996 | Lee | ...... | G06F 17/5077 716/119 |
| 5,822,214 A * | 10/1998 | Rostoker | ...... | G06F 17/5072 716/123 |
| 6,772,405 B1 * | 8/2004 | Gan | ...... | G06F 17/5068 703/18 |
| 8,191,034 B1 * | 5/2012 | Mohan | ...... | G06F 17/5081 716/136 |
| 8,762,910 B2 * | 6/2014 | Ohtsuka | ...... | G06F 17/5077 716/110 |
| 8,930,869 B2 * | 1/2015 | Ohtsuka | ...... | G06F 17/5077 716/126 |
| 9,348,963 B1 * | 5/2016 | Lin | ...... | G06F 17/5077 |

(Continued)

*Primary Examiner* — Helen Rossoshek
(74) *Attorney, Agent, or Firm* — Eric L. Sophir; Dentons US LLP

(57) ABSTRACT

Disclosed herein are embodiments of systems, methods, and products using a center access direction for pin figures during an abutment of instances in an integrated circuit (IC) design. Using a center access direction allows an electronic design automation (EDA) tool to overlap the centers of the pin figures to be merged. Once the centers of the pin figures are overlapped, the EDA tool runs one or more merging and optimization algorithms to abut the circuit devices containing the pin figures. The EDA tool therefore is computationally efficient and yet provides more functionality: unlike the conventional system, the EDA tool does not have to align the pin figures and calculate an offset to overlap the pin figures post alignment. Furthermore, the EDA tool can overlap the pin figures from any angle and is not confined to rectilinear access direction of the conventional systems.

20 Claims, 13 Drawing Sheets

(56) References Cited

U.S. PATENT DOCUMENTS

| 9,384,317 B1* | 7/2016 | Salowe | G06F 17/5081 |
|---|---|---|---|
| 2016/0085898 A1* | 3/2016 | Manohar | G06F 17/5068 |
| | | | 716/124 |
| 2017/0352623 A1* | 12/2017 | Chang | H01L 23/5283 |

* cited by examiner

Devices to be Abutted

METHODS AND SYSTEMS FOR CENTERING OF PINS DURING INSTANCE ABUTMENT

TECHNICAL FIELD

This application relates generally to the field of electronic circuit design, and more specifically methods and systems for customizable automated alignment of pins while abutting circuit devices represented within the design.

BACKGROUND

Modern semiconductor based integrated circuits (ICs) are incredibly complex and contain millions of circuit devices, such as transistors, and millions of interconnections between the circuit devices. Designing such complex circuits cannot be accomplished manually, and circuit designers use computer based Electronic Design Automation (EDA) tools for schematics, layouts, simulation, and verification of the complex circuits. Furthermore, EDA tools allow circuit designers to optimize a complex electronic circuit, for example, by reducing the footprints of the various circuit devices. The current version of Moore's law states that the number of transistors per square inch in an IC doubles every eighteen months. Reducing the footprint of transistors and other circuit devices, for example, by keeping them closer together will keep the pace of the explosive and exponential growth of computing power, as foreseen by Moore's law.

EDA tools typically use instances of programmable cells or parameterized cells (a single instance generally shortened as a "pcell") to form an electronic circuit design. The instances of pcells are connected through pins. For example, for a transistor pcell instance, the pins connecting the transistor pcell to other pcells in the design are a source pin, a drain pin, and a gate pin. A pin may include one or more connecting shapes, called pin figures. For the transistor pcell instance, a pin figure for the source pin may be rectangular. For optical fibers and transmission lines, a pin figure for the pins interconnecting the segments of the optical fibers and the transmission lines may be a circular.

An EDA tool may optimize an IC design by abutting pcell instances to reduce the device footprint of the pcell instances. In other words, the EDA tool may pack the pcell instances closer together or merge the pcells (by abutting) thereby saving valuable semiconductor space in the IC. For example, the EDA tool may detect that two pcell instances are sufficiently close to be abutted and may trigger an abutment process based on such detection. However, as described below, conventional EDA tools and pcell libraries are unnecessarily complex and computationally heavy and yet provide a restricted functionality.

FIG. 1A-1C show a conventional abutment process done by a conventional EDA tool. FIG. 1A shows two devices (transistors, as shown, each having a source pin S, drain pin D, and a gate pin) to be abutted together. Each of the devices has two rectilinear access directions, left and right. To abut these two devices, a conventional EDA tool first checks the access directions for the devices. The conventional EDA tool determines, based on these access directions, that the shown devices can be abutted such that the right edge of the device on the left can be aligned with the left edge of the device on the right. The conventional EDA tool then aligns the two devices as shown in FIG. 1B. More specifically, the drain pin D of the device on the left has been aligned with the source pin S on the device on the right. After the alignment, the conventional EDA tool calculates an offset for one or both of the aligned pins such that the aligned pins can be overlapped for further optimization. Based on the calculated offset, the conventional EDA tool overlaps the aligning pins as shown in FIG. 1C. The conventional EDA tool may then remove portions from one or more of the overlapped pins to generate the abutted optimized devices.

However, there are several technological problems with the conventional EDA tools employing the aforementioned steps. For instance, for every abutment, the conventional EDA tools have to undergo the edge alignment and make offset calculations to position pins for abutment, which makes the pcell library for the conventional EDA tools unnecessarily complex. Every pcell library must have an access direction for the edge alignment and have the code for calculating the offset for the overlapping. Using such a p-cell library is also computationally heavy because an EDA tool using that library has to align the devices and calculate the offset for every group of devices that are being abutted. In addition, the conventional approach is restrictive—it supports only rectilinear pin figure shapes because non-rectilinear shapes are not conducive to aligning by the steps discussed above. For example, two circular pin figure shapes will at best touch at a point and therefore will not align as the rectangular pin figures as described above. In addition, pin figure shapes having different sizes may not align with each other as the pin figure shapes described in FIGS. 1A-1C. Furthermore, the access directions in the conventional pcells are restricted to rectilinear x-y coordinates (right, left, top, and bottom), which is unable to provide an angular abutment. An angular abutment is crucial to ICs including photonics circuit devices such as fiber optic components and the conventional EDA therefore are unable to support abutting photonics circuit devices.

What is therefore required is a pcell library and EDA tools that solve the aforementioned problems of excess complexity and yet restricted functionality. What is therefore required is a simpler pcell library and EDA tools that use the pcell library for abutting any pin figure shape and size and at any angle.

SUMMARY

Embodiments disclosed herein solve the aforementioned problems and other problems by providing pcells with a center access direction as opposed to the rectilinear x-y directions. Having a center access directions allow EDA tools to skip the alignment and offset calculations. The offset calculation code therefore need not be embedded within the pcells, an abutment engine may abut the pcells without any offset calculations. The abutment engine may overlap the centers of the appropriate pin figures of the pcells to be abutted and run the abutment and optimization codes to abut the pin figures and remove portions from one or more pin figures. The EDA tools and the pcell library therefore are more computationally efficient and yet provide a better functionality.

In an embodiment, a computer implemented method for abutting circuit devices in an integrated circuit design comprises: receiving, by a computer, a plurality of database records of a plurality of circuit devices forming an integrated circuit (IC), wherein a first circuit device of the plurality of circuit devices includes a first set of pin figures and a second circuit device of the plurality of circuit devices includes a second set of pin figures; determining, by the computer, that a first pin figure of the first set of pin figures is to be overlapped with a second pin figure of the second set of pin figures based upon the location data of the first circuit device and the second circuit device in the respective database records; identifying, by the computer, a first center location of the first pin figure and a second center location of the second pin figure based on the location data of the first circuit device and the second circuit device in the respective database records; positioning, by the computer, at least one of the first circuit and second circuit devices such that the first center location and the second center location overlap; generating, by the computer, a third circuit device formed by abutting first and second circuit devices and having a portion formed by merging and optimizing the overlapping first and second pin figures; and updating, by the computer, the respective database records of the first and second circuit devices based on the transposing and the generating of the third circuit device formed by abutting first and second circuit devices.

In another embodiment, a system for abutting circuit devices in an integrated circuit design comprises: one or more computers comprising a non-transitory machine-readable media configured to store a plurality of database records of a plurality of circuit devices, wherein a first circuit device of the plurality of circuit devices includes a first set of pin figures and a second circuit device of the plurality of circuit devices includes a second set of pin figures; at least one computer of the one or more computers, the at least one computer coupled to the non-transitory machine readable media storing the plurality of database records and comprising a processor configured to: determine that a first pin figure of the first set of pin figures is to be overlapped with a second pin figure of the second set of pin figures based upon the location data of the first circuit device and the second circuit device in the respective database records; identify a first center location of the first pin figure and a second center location of the second pin figure based on the location data of the first circuit device and the second circuit device in the respective database records; position at least one of the first circuit and second circuit devices such that the first center location and the second center location overlap; generate a third circuit device formed by abutting first and second circuit devices and having a portion formed by merging and optimizing the overlapping first and second pin figures; and update the respective database records of the first and second circuit devices based on the transposing and the generating of the third circuit device formed by abutting first and second circuit devices.

BRIEF DESCRIPTION OF THE DRAWINGS

The accompanying drawings constitute a part of this specification and illustrate embodiments of the subject matter disclosed herein.

DETAILED DESCRIPTION

Figure 1A:
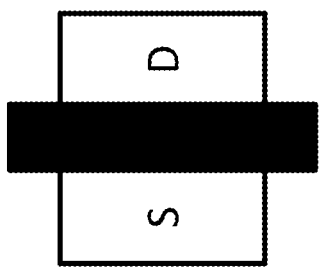
FIGS. 1A-1C show a conventional overlapping of pin figures based on rectilinear access direction.
Figure 1A:
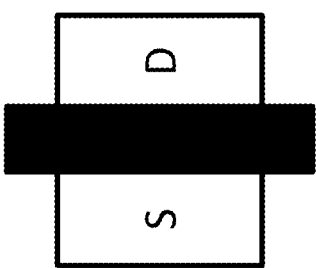
Figure 1B:
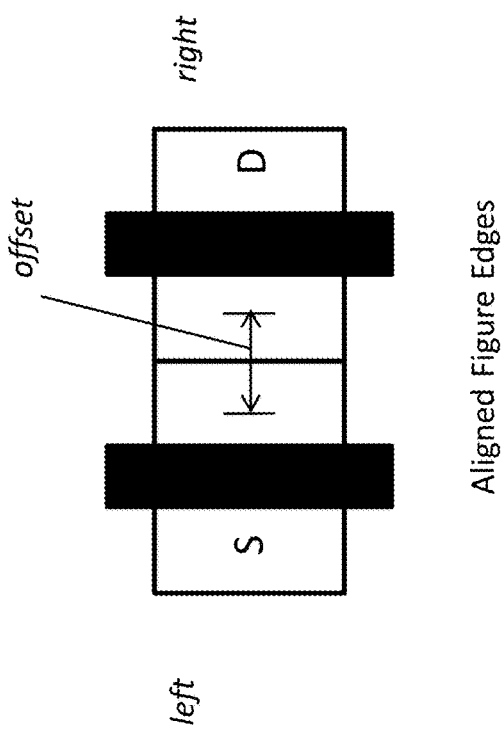
Figure 1C:
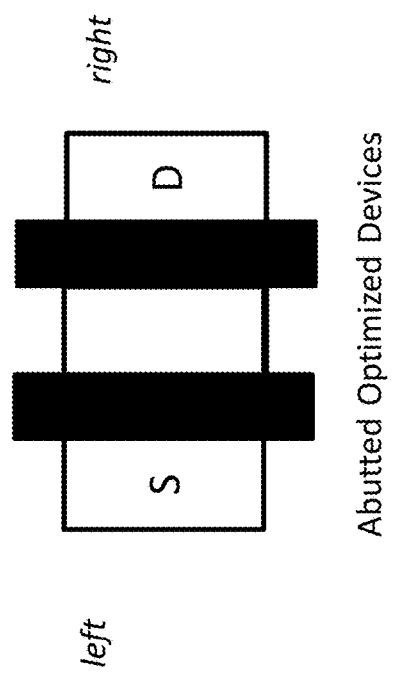

Reference will now be made to the illustrative embodiments illustrated in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one ordinarily skilled in the relevant art and having possession of this disclosure, are to be considered within the scope of the subject matter disclosed herein. The present disclosure is here described in detail with reference to embodiments illustrated in the drawings, which form a part here. Other embodiments may be used and/or other changes may be made without departing from the spirit or scope of the present disclosure. The illustrative embodiments described in the detailed description are not meant to be limiting of the subject matter presented here.

Embodiments of the systems, products and methods disclosed herein provide a computationally efficient and yet a flexible approach for centering of pins while abutting pcell instances. Although the disclosure is described in terms of pcell instances, one having ordinary skill in the art understands that the disclosure is equally applicable to fixed cell instances. Furthermore, one having ordinary skill in the art understands that pcells and pcell instances or fixed cells or fixed cell instances can be used interchangeably. As discussed above, the conventional systems that use rectilinear access direction are computationally inefficient and yet are unduly restricted. For example, conventional systems have to align the pin figures to be merged and calculate an offset to overlap the pin figures. Aligning the pin figures is not conducive to merging pins having a circular or a conic figure such as circular pins in optical waveguides. In addition, the pin figures may be different sizes and therefore cannot be aligned. Furthermore, the conventional systems are confined to using rectilinear access direction, which cannot handle overlapping at an angle.

In contrast to the conventional system, the embodiments discussed herein disclose an electronic design automation (EDA) tool and pcells that use a center access direction. An abutment engine in the EDA tool may use the center access direction to overlap the pin figures to be merged without undergoing the process of alignment and calculating an offset after alignment. The automation engine may transpose or reposition the pcells to be abutted such the centers of the pin figures to be merged are overlapping after the transpose or reposition. The automation engine may then execute one or more merging and optimization algorithm to abut the pcells by merging the overlapped pin figures. The automation engine may optimize the overlapping pin figures by removing portions from at least one of the overlapping pin figures. In some embodiments, the EDA tool may combine rectilinear access direction with the center access direction. Using the rectilinear access direction, the EDA tool may identify the pin figures to be merged in the pcells to be abutted. The EDA tool may then use the center access direction to overlap the pin figures to be merged.

Figure 2:
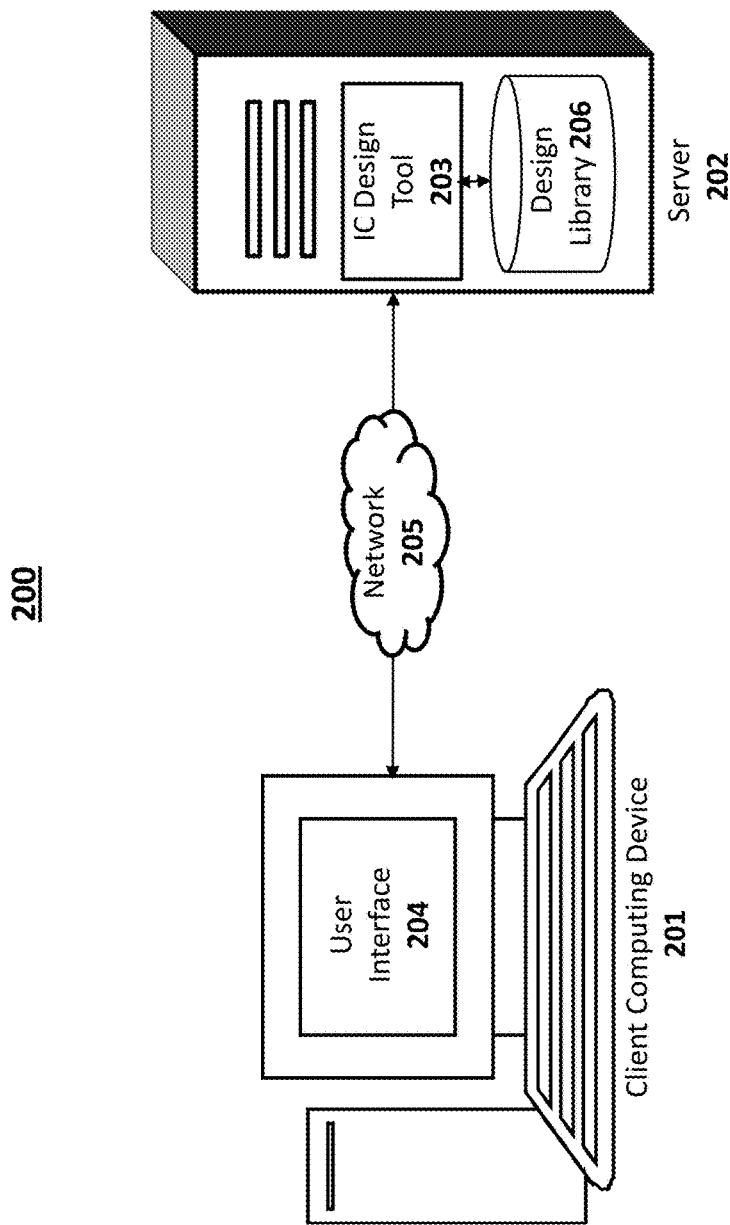
FIG. 2 shows an exemplary system for centering of pins during instance abutment, according to an exemplary embodiment.

FIG. 2 illustrates an electronic design automation system 200, according to an exemplary embodiment. The electronic design automation system 200 may include any number of computing devices; the exemplary embodiment may include a client computing device 201 and a server 202. One or more components of the electronic design automation system 200 may be grouped and referred to as an electronic design automation tool (or EDA tool). The client 201 may be connected to the server 202 via hardware and software components of one or more networks 205. In some embodiments, the system 200 may be a cloud-based system wherein one or more functionalities of the system 200 may be performed by one or more cloud computing devices. A network 205 may also connect various computing devices with databases or other components of the system 200. Examples of the network 205 include, but are not limited to, Local Area Network (LAN), Wireless Local Area Network (WLAN), Metropolitan Area Network (MAN), Wide Area Network (WAN), and the Internet. The communication over the network 205 may be performed in accordance with various communication protocols, such as Transmission Control Protocol and Internet Protocol (TCP/IP), User Datagram Protocol (UDP), and IEEE communication protocols.

A client device 201 may be any computing device comprising a processor/microcontroller and/or any other electronic component that performs one or more operations according to one or more programming instructions. The examples of the computing device may include, but are not limited to, a desktop computer, a laptop, a personal digital assistant (PDA), a smartphone, a tablet computer, and the like. The client device 201 may be configured to communicate with one or more servers 202 of the system 200 through one or more networks 205, using wired and/or wireless communication capabilities. A user interface 204 may include a Graphical User Interface (GUI) that renders an interactive, graphical representation of an IC design, layout, schematic, or other logical representation of an IC that is being designed and optimized using an IC design tool 203. The GUI 204 may provide interactive elements, such as graphical representations of IC design elements (e.g., pcell instances), for a user to manipulate the IC design layout. In some embodiments, the user interface 204 may include a text based interface allowing the user to enter manual commands for designing and optimizing the IC.

A server 202 may be accessible to the client device 201 via one or more networks 205. The server 202 may be any computing device comprising a processor and other computing hardware configured to execute an IC design tool 203 software module (e.g., EDA design software) that may analyze and optimize an IC design. In operation, using a client device 201 to access a design tool 203 hosted on a server 202 over a network 205, a circuit designer may interact with the IC design tool 203, through a number of input devices of the client device 201, such as by inputting a selection as with a mouse or inputting a request as with a keyboard. The IC design tool 203 may generate any number of graphical interface 204 responses based on the inputs received from the client device 201, and then send the data back to the client device 201 to be rendered on the GUI 204.

The server 202 may execute one or more component software modules of the IC design tool 203 software program, which may be a software program that allows users (e.g., engineers, circuit designers) to design and optimize circuit designs through software modules. The IC design tool 203 may provide users with interactive design interfaces 204 for designing an IC and the various design elements, execute automated optimization processes, and execute automated layout-generation processes. The server 202 may comprise, or may be in networked-communication with, non-transitory machine-readable media configured to store a netlist of or any other file including records of IC design elements, which may be a machine-readable computer file or a design database containing one or more records of design elements (e.g., circuit devices, pcells) of the IC design. In operation, the IC design tool 203 may analyze and optimize the design elements of the netlist or any other type of file associated with the IC design. Non-limiting examples of circuit devices may include memory devices (e.g., flops), combination logic gates (e.g., AND, OR, NOT, NOR, NAND, XOR), and multiplexers, among others. The netlist or any other type of file may also include records of a plurality of nets. The nets may be the records associated with the wires interconnecting the plurality of circuit devices.

The server 202 may include a design library 206 that is accessed by the IC design tool 203. The design library 206 may include instances of various circuit devices, for example, transistors used to layout an IC. In some embodiments, the design library 206 may include instances of pcells used by the IC design tool 203 to generate an IC layout. An instance of a pcell may represent electronic circuit components such as a transistor, transmission line, or an optical fiber line. The IC design tool 203 may use instances of pcells in the design library 206 to generate a netlist of an IC that can be sent to a manufacturing facility for fabrication.

The exemplary system 200 is shown in FIG. 2 as comprising only one server 202 for ease of explanation. However, it should be appreciated that the system 200 may comprise a number of servers 202. In some embodiments, the system 100 may comprise multiple interconnected, networked servers 202, some of which may execute various software modules configured to manage and control the resources and performance of the system 200. In some embodiments, the servers 202 may have parallel architectures configured to support multi-threading on multi-core workstations to handle large designs. In such embodiments, the servers 202 may be configured for distributed processing. The server 202 may be logically and physically organized within the same or different devices or structures, and may be distributed across any number of physical structures and locations (e.g., cabinets, rooms, buildings, cities).

In operation, the exemplary system 200 may identify pcell instances to be abutted. The exemplary system 200 may further identify, in the pcell instances, the pin figures to be merged. The exemplary system 200 may determine the center locations of the pin figures and transpose or reposition the pcell instances such that the center locations of the pin figures overlap. The exemplary system 200 may execute one or more merging and optimization codes on the overlapped pin figures to abut the pcell instances.

Figure 3:
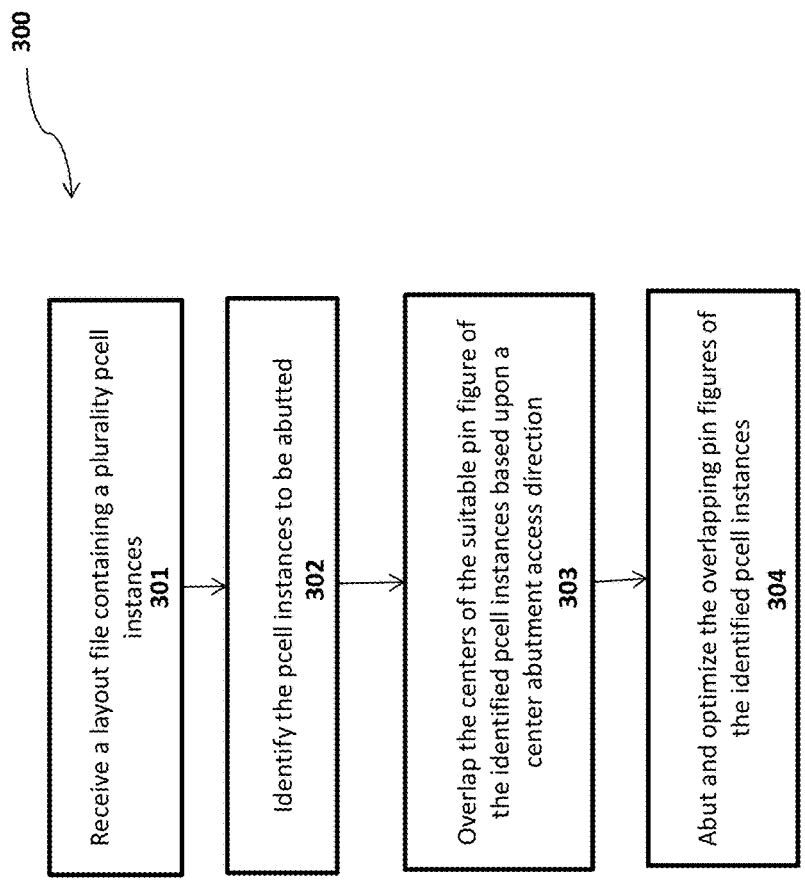
FIG. 3 shows an exemplary method for centering of pins during instance abutment, according to an exemplary embodiment.

FIG. 3 shows an exemplary method 300 for centering of pins during instance abutment, according to an exemplary embodiment. Although one or more computing devices and one or more databases may implement one or more steps of the method 300, the following description details, for brevity, a computer system implementing the steps of the method 300. One having skill in the art will appreciate that some embodiments may comprise additional or alternative steps, or may omit several steps altogether.

In a first step 301, the computer system may receive a layout file containing a plurality of pcell instances. In some embodiments, a circuit designer may upload the layout file into the memory of the computer system. In other embodiments, a circuit designer may use a graphical user interface (GUI) layout to instantiate and use various pcells to generate a graphical circuit layout. The computer system may generate the layout file based on the graphical circuit layout. The plurality of pcell instances may be distributed across various layers of the circuit being designed. Furthermore, a single pcell instance may span multiple layers of the circuit being designed. Non-limiting examples of circuit components represented by a pcell instance may include transistors, transmission lines, resistors, fiber optic components, and inductors. Although this disclosure describes pcell instances, fixed cells are also considered to be within the scope of the disclosure.

In a next step 302, the computer system may identify the pcell instances to be abutted. In some embodiments, the computer system may determine, based on the location of the pcells as stored in the memory of the computer or in a database file such as a netlist, that the pcells are closer together in the layout and therefore should be abutted. For example, a circuit designer may place two pcell instances very close in a layout, which may trigger the computer system to execute an abutment engine on the two pcell instances. In other embodiments, the circuit designer may identify to the computer system, either through a command line interface or a GUI, the pcell instances to be abutted. Based on the circuit designer's input, the computer system may execute the abutment on the identified pcell instances. In some embodiments, the computer system may determine that two or more pcell instances are overlapping and execute an abutment engine on the two or more overlapping pcell instances.

In a next step 303, the computer system may overlap the centers of the suitable pin figures of the identified pcell instances based upon a center abutment access direction. The computer system may select the suitable pin figures based on the relative orientation of the pcell instances. For example, for pcells horizontally next to each other, the computer system may select the pin figures at the right of a pcell on the left, and pin figures at the left of the pcell on the right. As another example, for pcells vertically next to each other, say a first pcell on the top and a second pcell at the bottom, the computer system may select the pin figures at the bottom of the first pcell and the pin figures at the top of the second pcell. For angular orientation, for example, the pcell instances facing each other at an angle, the computer system may select the pin figures facing each other. The center abutment access direction may allow the computer system to implement an alignment agnostic abutment, that is, with the center abutment access direction, the computer system does not have to align and then offset the pin figures. In addition to the relative orientation of the pcell instances, the computer system may select the suitable pin figures based on the net connectivity of the pin figures. For example, the computer system may select the pin figures connected to same nets and/or same instances in the circuit.

The computer system may overlap the centers of the identified pcell instances. For instance, the computer system may query the respective database records, in a memory or a storage, of the identified pcell instances to determine the location of the center of the pin figures to be abutted. For instance, the computer system may determine the location of the center of a first pin figure of a first pcell instance to be and X and the location of the center of a second pin figure of a second pcell instance to be Y. Based on factors such as other pcell instances in the immediate vicinity of the first and second pcell instances, the computer system may move the first pcell or the second pcell such that the centers of the first and second pin figures overlap. For example, the computer system may move the first pcell instance such that the first and second pin figures overlap at Y, or the computer system may move the second pcell instance such that first and second pin figures overlap at X. Alternatively, the computer system may move both the first and the second pcell instances such that the first and second pin figures overlap at a location between X and Y. One having ordinary skill in the art appreciates that the computer system may move the pcell instances rectilinearly or at an angle, thereby allowing flexibility in the abutment process. Based on moving one or more of the first and second pcells, the computer system may update the database records of the first and/or second pcells.

In a next step 304, the computer system may abut and optimize the overlapping pin figures of the identified pcell instances. In some instances, the computer system may determine that the overlapping pin figures are connected to same nets and/or same instances in the circuit. Based on this determination, the computer system may merge the overlapping pin figures. In some implementations, the computer system may determine that the portions of the overlapping pins are redundant and may remove the redundant portions based on such determination thereby reducing the overall device footprint of the abutted pcell instances.

Figure 4A:
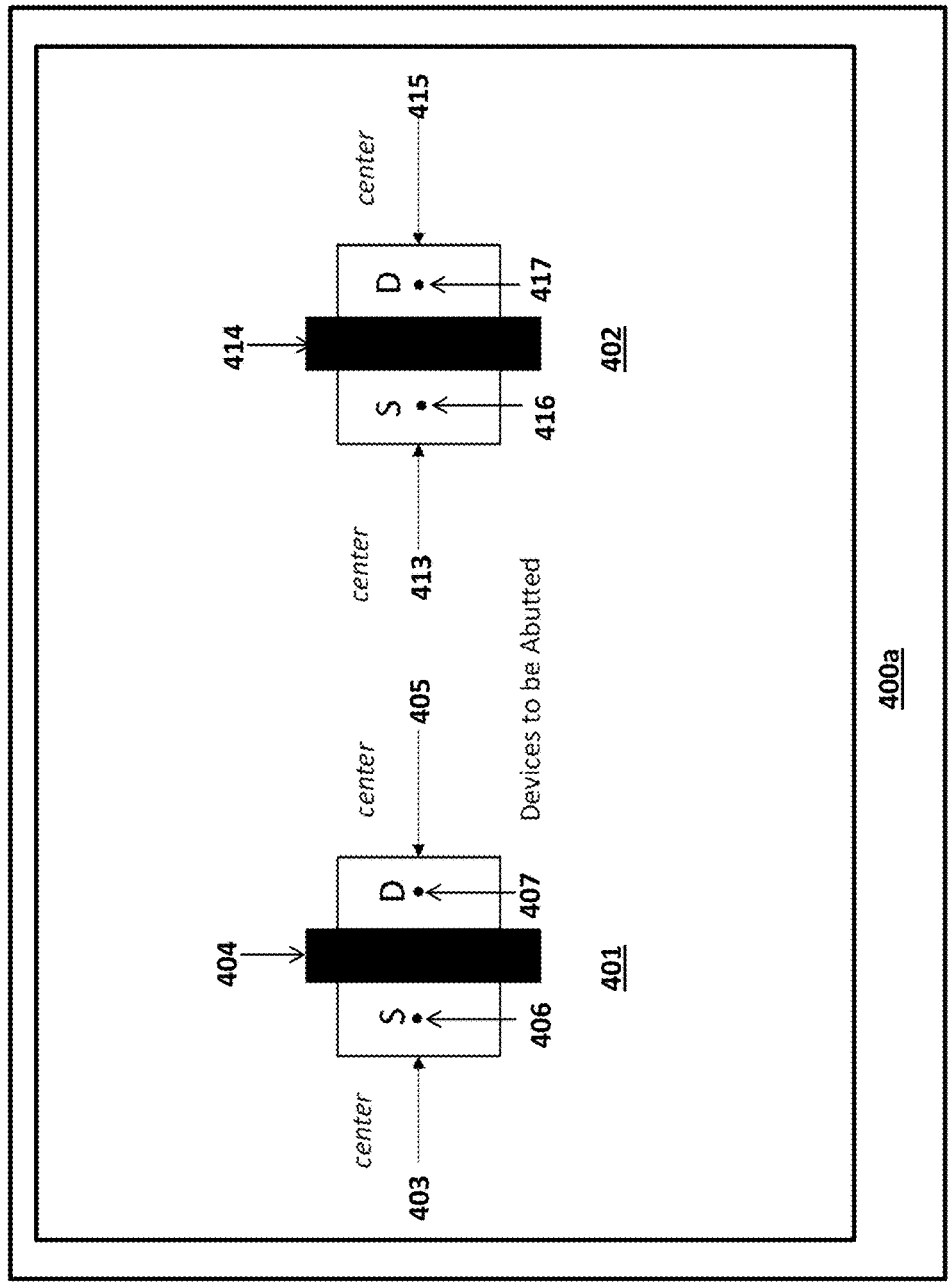
FIG. 4A shows an exemplary GUI rendering two circuit devices to be abutted, according to an exemplary embodiment.

FIG. 4A shows an exemplary GUI 400a generated by an electronic design automation (EDA) tool executing centering of pins during instance abutment, according to an exemplary embodiment. The GUI 400a shows a first pcell instance 401 and a second pcell instance 402. As shown, each of the pcell instances 401, 402 may represent a transistor. The first pcell instance 401 may contain three pin figures 403, 404, 405, and the second pcell instance may contain three pin figures 413, 414, 415. In the first pcell instance 401, the center for the pin FIG. 403 may be 406 and the center of the pin figure 405 may be 407. In the second pcell instance 402, the center for the pin figure 413 may be 416 and the center of the pin figure 415 may be 417. The EDA tool may determine that the first pcell instance 401 and the second pcell instance 402 should be abutted based on the proximity of the first and second pcell instances 401, 402 and/or based on an input from a circuit designer. The EDA tool may execute an abutment engine based on the center access direction of the first and second pcell instances 401, 402. The abutment engine may determine, based on the relative orientation of the first and second pcell instances that the pin figure 405 should be abutted with pin figure 413. The abutment engine may then use the center access direction to overlap the center 407 of the pin figure 405 with the center 416 of the pin figure 413. The abutment engine may execute one or more optimization algorithms to merge and or optimize away portions of the pin figures 405, 413.

Figure 4B:
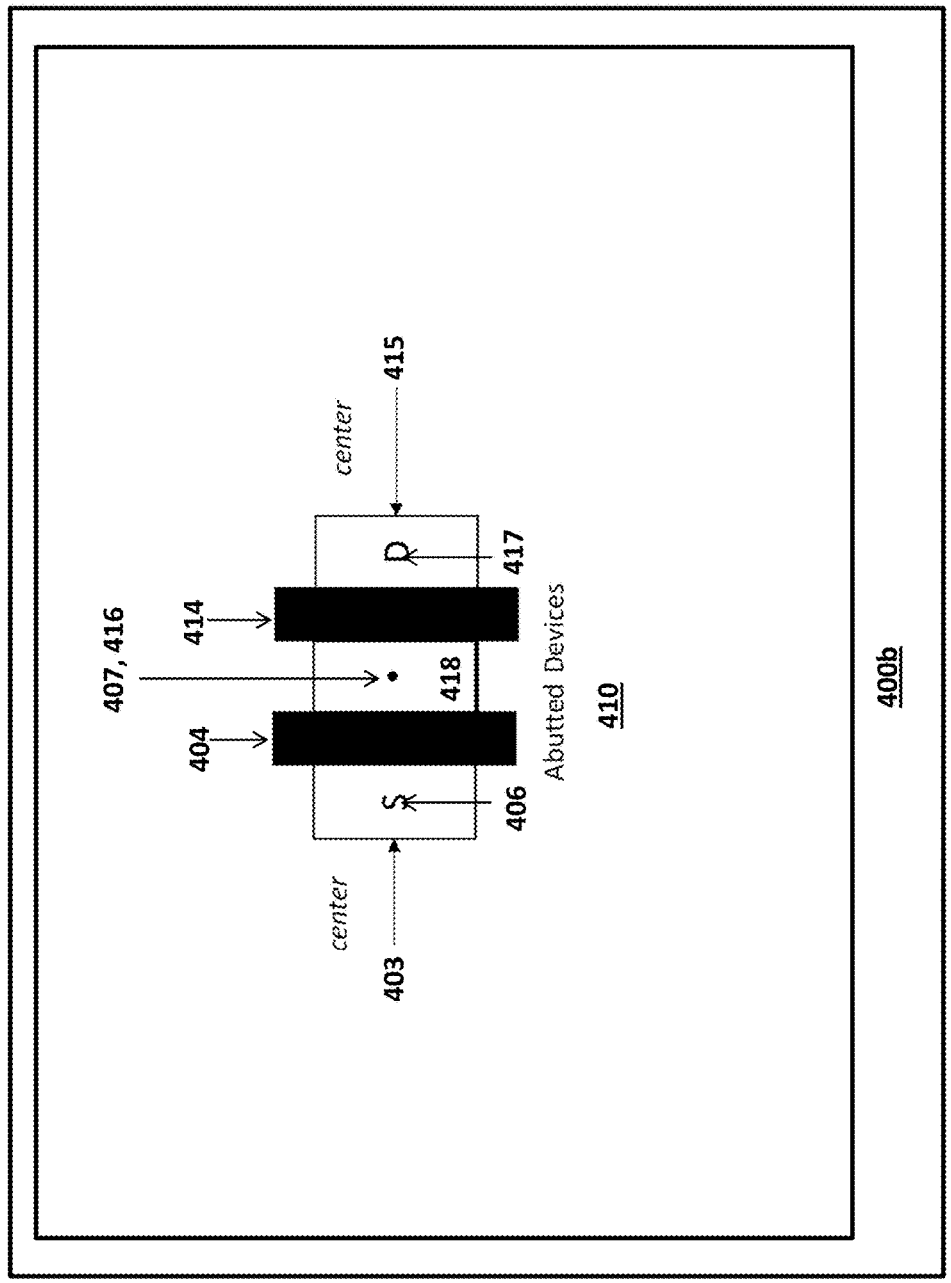
FIG. 4B shows an updated exemplary GUI showing abutted circuit devices, according to an exemplary embodiment.

FIG. 4B shows an updated exemplary GUI 400b generated by the EDA tool after the abutment process. As shown in the updated GUI 400b, the EDA tool has abutted the first and second pcell instances 401, 402 to generate an abutted pcell instance 410. Although this disclosure refers to the abutted pcell instance 410 in a singular form, one having ordinary skill in the art understands the abutted pcell instance 410 contains two abutted pcell instances. To abut the first and second pcell instances 401, 402, the EDA tool has abutted pin figures 405, 413 to generate the abutted portion 418. Also shown in the GUI are overlapping centers of 407, 416 of the pin figures 405, 413. Based on the aforementioned abutment the EDA tool may update the respective database records of the first and second pcells 401, 402.

Figure 5A:
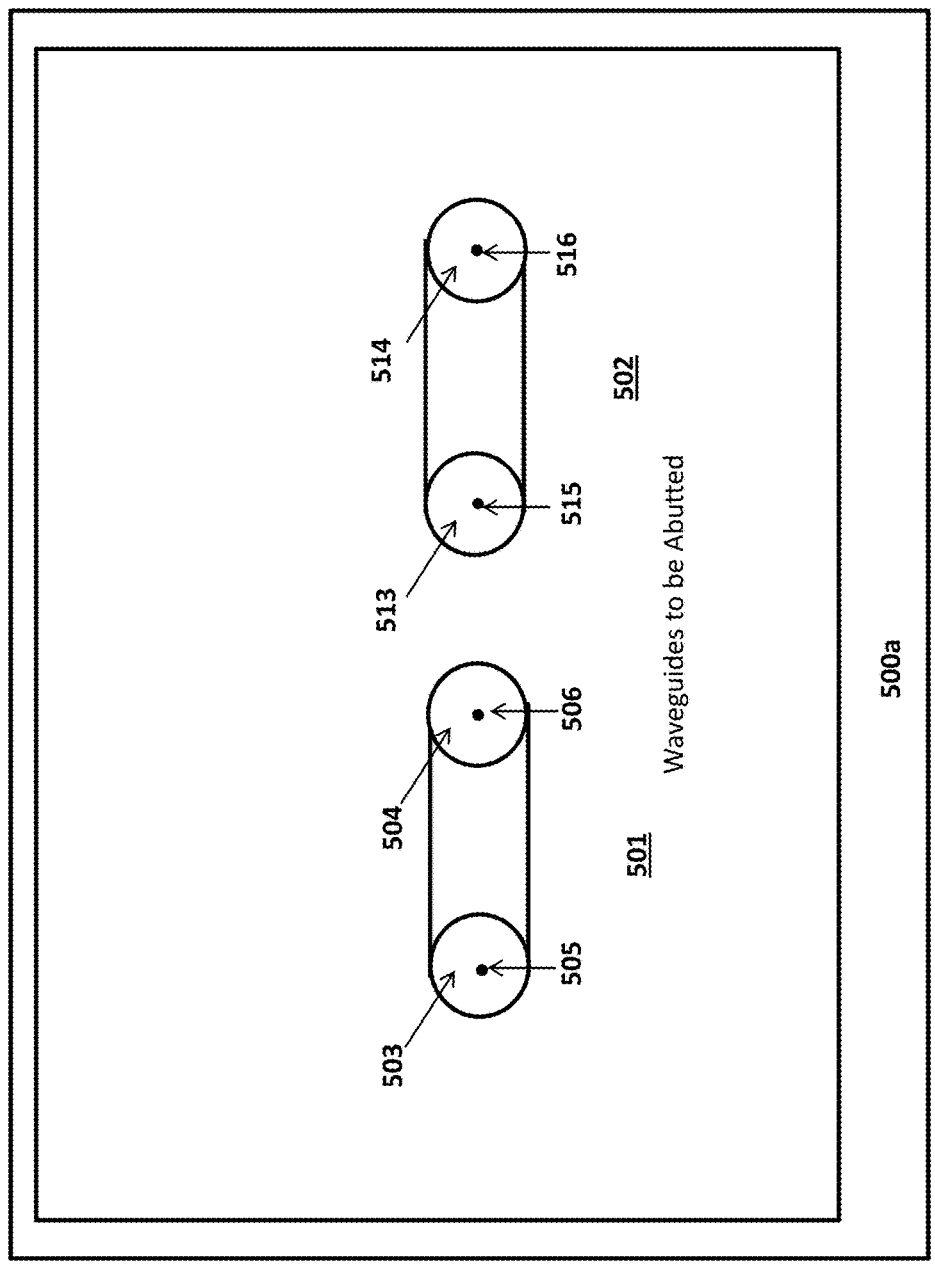
FIG. 5A shows an exemplary GUI rendering two waveguides to be abutted, according to an exemplary embodiment.

FIG. 5A shows an exemplary GUI 500a generated by an electronic design automation (EDA) tool executing centering of pins during instance abutment, according to an exemplary embodiment. The GUI 500a shows a first pcell instance 501 and a second pcell instance 502. As shown, each of the pcell instances 501, 502 may represent an optical waveguide. The first pcell instance 501 may contain two pin figures 503, 504, and the second pcell instance may contain two pin figures 513, 514. In the first pcell instance 501, the center for the pin figure 503 may be 505 and the center of the pin figure 504 may be 506. In the second pcell instance 502, the center for the pin figure 513 may be 515 and the center of the pin figure 514 may be 516. The EDA tool may determine that the first pcell instance 501 and the second pcell instance 502 should be abutted based on the proximity of the first and second pcell instances 501, 502 and/or based on an input from a circuit designer. The EDA tool may execute an abutment engine based on the center access direction of the first and second pcell instances 501, 502. The abutment engine may determine, based on the relative orientation of the first and second pcell instances that the pin figure 504 should be abutted with pin figure 513. The abutment engine may then use the center access direction to overlap the center 506 of the pin figure 504 with the center 515 of the pin figure 513. The abutment engine may execute one or more optimization algorithms to merge and or optimize away portions of the pin figures 504, 513.

Figure 5B:
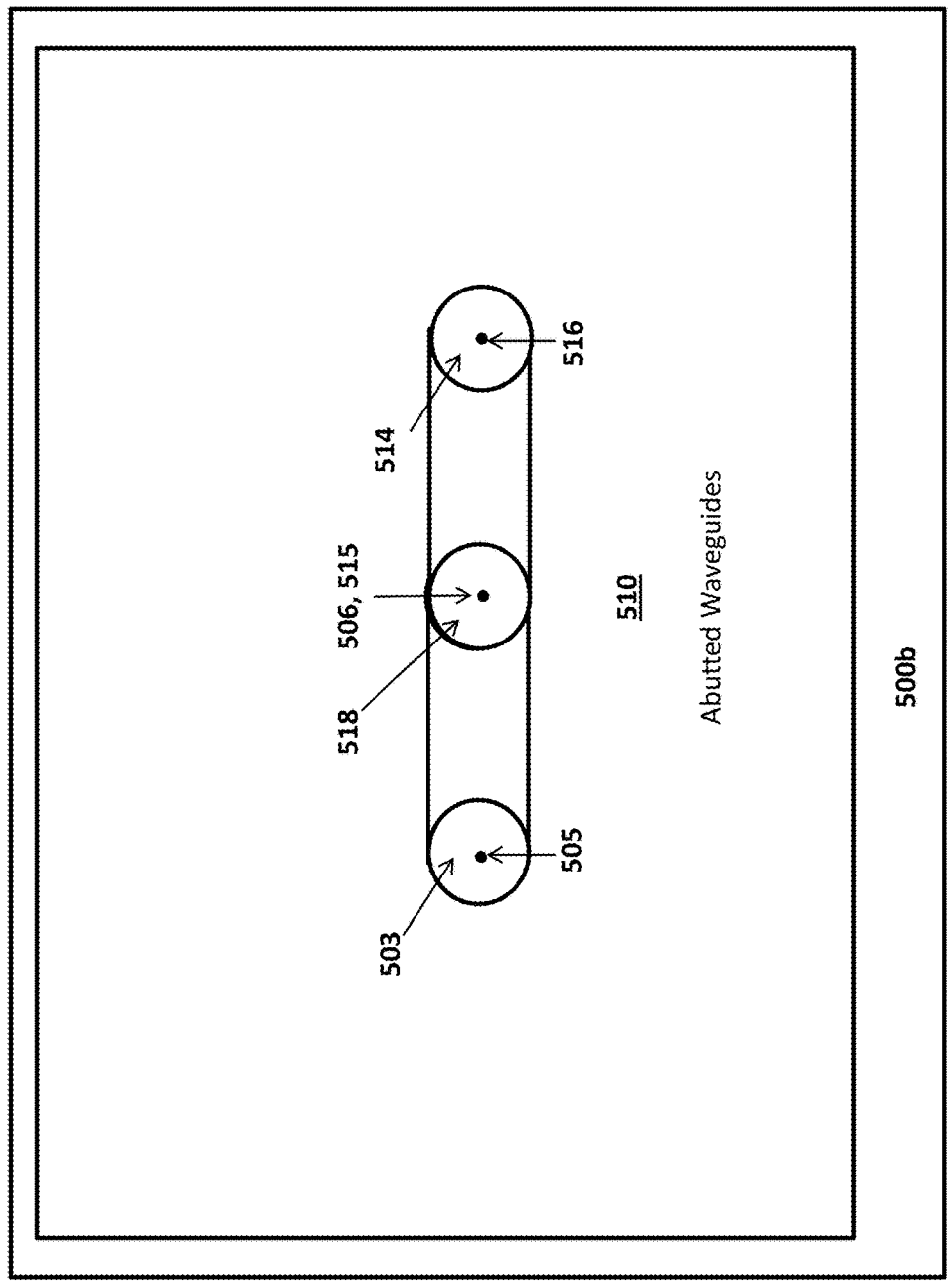
FIG. 5B shows an updated exemplary GUI showing abutted waveguides, according to an exemplary embodiment.

FIG. 5B shows an updated exemplary GUI 500b generated by the EDA tool after the abutment process. As shown in the updated GUI 500b, the EDA tool has abutted the first and second pcell instances 501, 502 to generate an abutted pcell instance 510. Although this disclosure refers to the abutted pcell instance 510 in a singular form, one having ordinary skill in the art understands the abutted pcell instance 510 contains two abutted pcell instances. To abut the first and second pcell instances 501, 502, the EDA tool has abutted pin figures 504, 513 to generate the abutted portion 518. Also shown in the GUI are overlapping centers of 506, 515 of the pin figures 504, 513. Based on the aforementioned abutment the EDA tool may update the respective database records of the first and second pcells 501, 502. The abutment described generates a combined continuous optical waveguide. Although this embodiment describes abutting optical waveguides, one having ordinary skill in the art appreciates that the EDA tool may execute similar steps to abut radio frequency (RF) transmission lines.

Figure 6A:
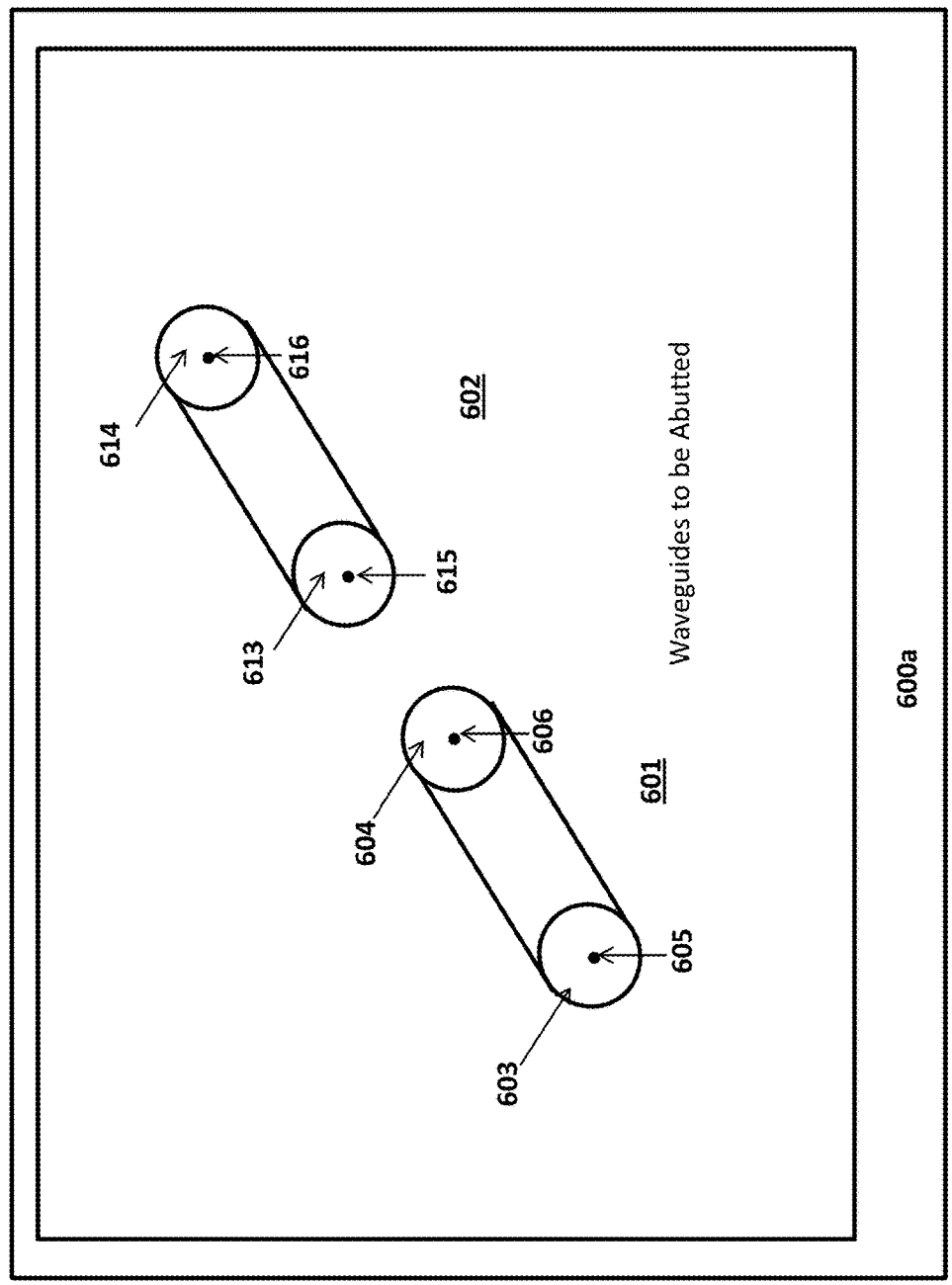
FIG. 6A shows an exemplary GUI rendering two waveguides to be abutted from an angle, according to an exemplary embodiment.

FIG. 6A shows an exemplary GUI 600a generated by an electronic design automation (EDA) tool executing centering of pins during instance abutment, according to an exemplary embodiment. The GUI 600a shows a first pcell instance 601 and a second pcell instance 602. As shown, each of the pcell instances 601, 602 may represent a waveguide. The first pcell instance 601 may contain two pin figures 603, 604, and the second pcell instance may contain two pin figures 613, 614. In the first pcell instance 601, the center for the pin figure 603 may be 605 and the center of the pin figure 604 may be 606. In the second pcell instance 602, the center for the pin figure 613 may be 615 and the center of the pin figure 614 may be 616. The EDA tool may determine that the first pcell instance 601 and the second pcell instance 602 should be abutted based on the proximity of the first and second pcell instances 601, 602 and/or based on an input from a circuit designer. The EDA tool may execute an abutment engine based on the center access direction of the first and second pcell instances 601, 602. The abutment engine may determine, based on the relative orientation of the first and second pcell instances that the pin figure 604 should be abutted with pin figure 613. The abutment engine may then use the center access direction to overlap the center 606 of the pin figure 604 with the center 615 of the pin figure 615. The abutment engine may execute one or more optimization algorithms to merge and or optimize away portions of the pin figures 604, 613.

Figure 6B:
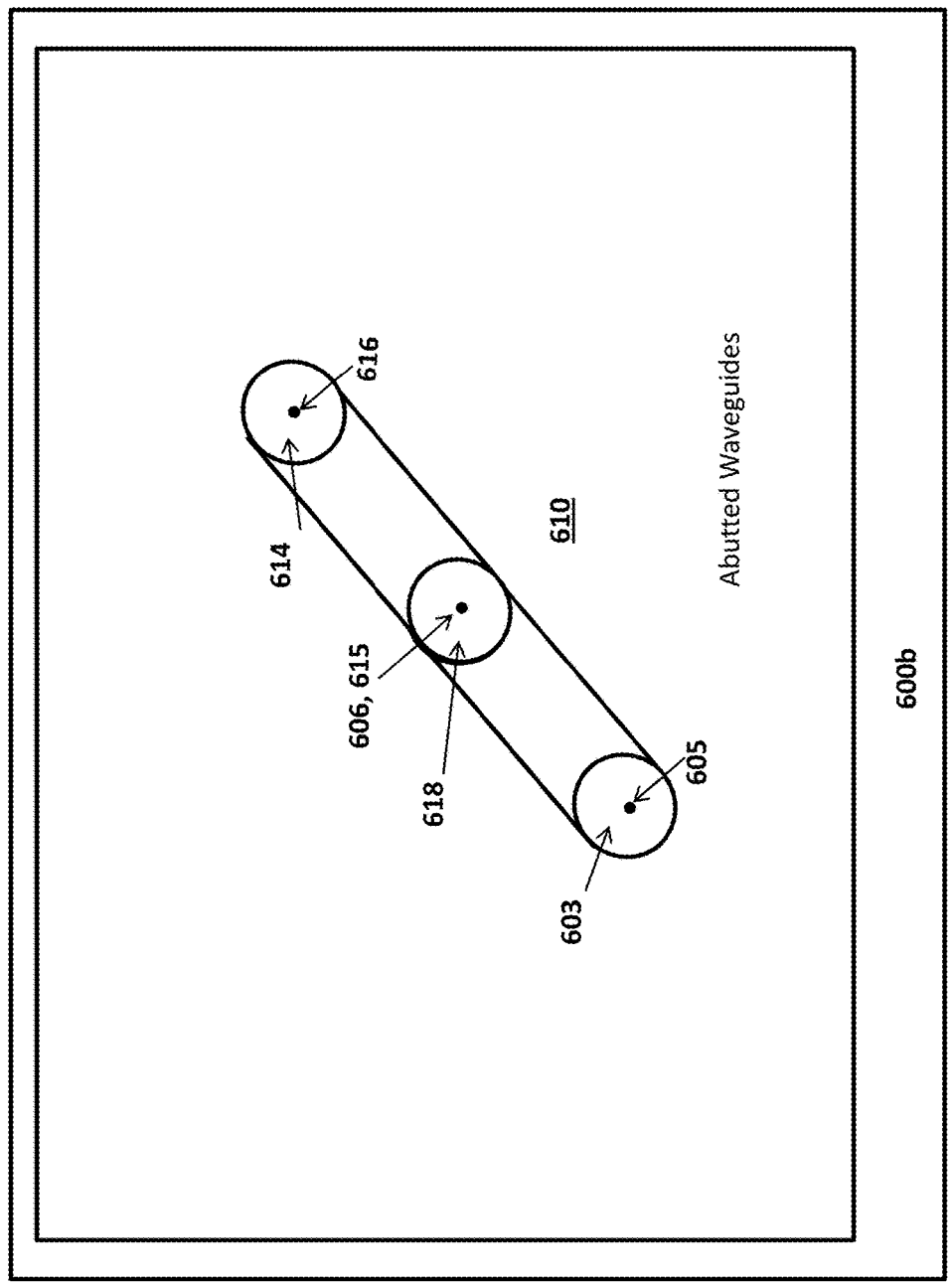
FIG. 6B shows an updated exemplary GUI showing abutted waveguides, according to an exemplary embodiment.

FIG. 6B shows an updated exemplary GUI 600b generated by the EDA tool after the abutment process. As shown in the updated GUI 600b, the EDA tool has abutted the first and second pcell instances 601, 602 to generate an abutted pcell instance 610. Although this disclosure refers to the abutted pcell instance 610 in a singular form, one having ordinary skill in the art understands the abutted pcell instance 610 contains two abutted pcell instances. To abut the first and second pcell instances 601, 602, the EDA tool has abutted pin figures 604, 613 to generate the abutted portion 618. Also shown in the GUI are overlapping centers of 606, 615 of the pin figures 604, 613. Based on the aforementioned abutment the EDA tool may update the respective database records of the first and second pcells 601, 602. As seen from in this embodiment, the EDA tool may abut the pcell instances 601, 602 from any angle, and unlike the conventional system, this abutting process is not confined to rectilinear alignment and merging. The abutment process described herein generates a combined and continuous waveguide. Although this embodiment describes abutting optical waveguides, one having ordinary skill in the art appreciates that the EDA tool may execute similar steps to abut radio frequency (RF) transmission lines.

Figure 7A:
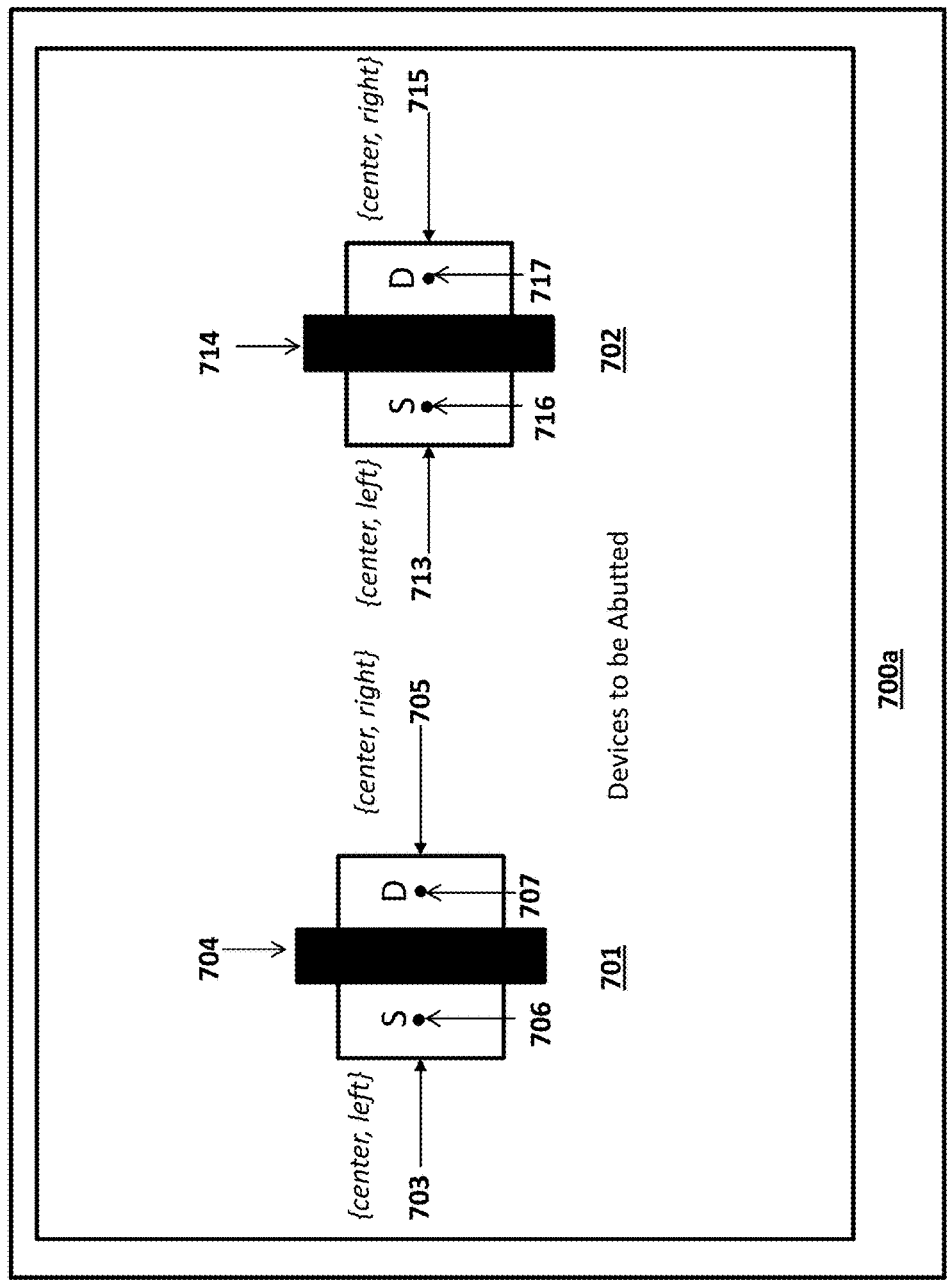
FIG. 7A shows an exemplary GUI rendering two circuit devices to be abutted using a combination of a center access direction and a rectilinear access direction, according to an exemplary embodiment.

FIG. 7A shows an exemplary GUI 700a generated by an electronic design automation (EDA) tool executing centering of pins during instance abutment, according to an exemplary embodiment. The EDA tool may generate the GUI 700a when the EDA tool uses a combination of rectilinear access directions (left, right, top, and bottom) combined with the center access direction. The GUI 700a shows a first pcell instance 701 and a second pcell instance 702. As shown, each of the pcell instances 701, 702 may represent a transistor. The first pcell instance 701 may contain three pin figures 703, 704, 705, and the second pcell instance may contain three pin figures 713, 714, 715. In the first pcell instance 701, the center for the pin figure 703 may be 706 and the center of the pin figure 705 may be 707. In the second pcell instance 702, the center for the pin figure 713 may be 716 and the center of the pin figure 715 may be 717. The EDA tool may determine that the first pcell instance 701 and the second pcell instance 702 should be abutted based on the proximity of the first and second pcell instances 701, 702 and/or based on an input from a circuit designer. The EDA tool may execute an abutment engine based on the center access direction of the first and second pcell instances 701, 702. The abutment engine may determine, based on the rectilinear access directions for the pcell instances 701, 702 that pin figure 705 of the pcell instance 701 should be merged with pin figure 713 of the pcell instance 702. The abutment engine may then use the center access direction to overlap the center 707 of the pin figure 705 with the center 716 of the pin figure 413. The abutment engine may execute one or more optimization algorithms to merge and or optimize away portions of the pin figure 705, 713.

Figure 7B:
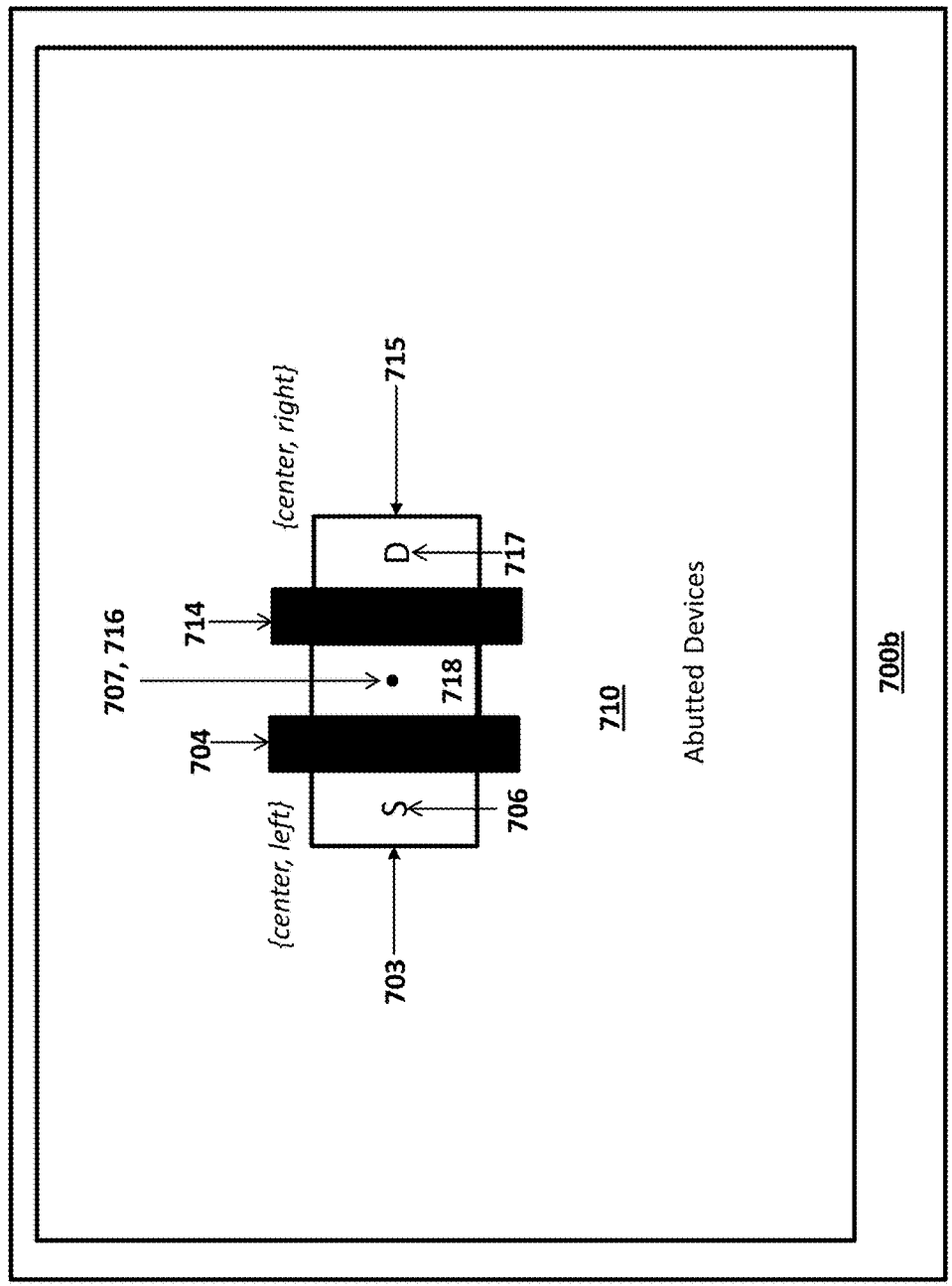
FIG. 7B shows an updated exemplary GUI showing abutted circuit devices, according to an exemplary embodiment.

FIG. 7B shows an updated exemplary GUI 700b generated by the EDA tool after the abutment process. As shown in the updated GUI 700b, the EDA tool has abutted the first and second pcell instances 701, 702 to generate an abutted pcell instance 710. Although this disclosure refers to the abutted pcell instance 710 in a singular form, one having ordinary skill in the art understands the abutted pcell instance 710 contains two abutted pcell instances. To abut the first and second pcell instances 701, 702, the EDA tool has abutted pin figures 705, 713 to generate the abutted portion 718. Also shown in the GUI are overlapping centers of 707, 716 of the pin figures 705, 713. Based on the aforementioned abutment the EDA tool may update the respective database records of the first and second pcells 701, 702. One having ordinary skill in the art understands that this embodiment combines the rectilinear access direction with the center access direction.

The foregoing method descriptions and the process flow diagrams are provided merely as illustrative examples and are not intended to require or imply that the steps of the various embodiments must be performed in the order presented. The steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, and the like. When a process corresponds to a function, the process termination may correspond to a return of the function to a calling function or a main function.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the generic principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A computer implemented method for abutting circuit devices in an integrated circuit design, the method comprising:
receiving, by a computer, a plurality of database records of a plurality of circuit devices forming an integrated circuit (IC), wherein a first circuit device of the plurality of circuit devices includes a first set of pin figures and a second circuit device of the plurality of circuit devices includes a second set of pin figures;
determining, by the computer, that a first pin figure of the first set of pin figures is to be overlapped with a second pin figure of the second set of pin figures based upon the location data of the first circuit device and the second circuit device in the respective database records;
identifying, by the computer, a first center location of the first pin figure and a second center location of the second pin figure based on the location data of the first circuit device and the second circuit device in the respective database records;
positioning, by the computer, at least one of the first circuit and second circuit devices such that the first center location and the second center location overlap;
generating, by the computer, a third circuit device formed by abutting first and second circuit devices and having a portion formed by merging and optimizing the overlapping first and second pin figures; and
updating, by the computer, the respective database records of the first and second circuit devices based on the generating of the third circuit device formed by abutting first and second circuit devices, whereby the computer provides a computationally efficient and a flexible centering of the first and second pin figures.

2. The method of claim 1, wherein at least one of the first and second circuit devices is represented by a pcell instance.

3. The method of claim 1, wherein at least one of the first and second circuit devices is represented by a first fixed cell instance.

4. The method of claim 1, wherein at least one of the first and second circuit devices is a transistor.

5. The method of claim 1, wherein at least one of the first and second circuit devices is an optical waveguide or a radio frequency (RF) transmission line.

6. The method of claim 1, further comprising:
determining, by the computer, that the first pin figure of the first set of pin figures is to be overlapped with the second pin figure of the second set of pin figures based upon rectilinear access directions of the first and second pin figures.

7. The method of claim 1, further comprising:
automatically identifying, by the computer system, that the first and second circuit devices from the plurality of circuit devices are to be abutted based on the proximity of the first and second devices determined based on location data of the first and second circuit devices in the respective database records.

8. The method of claim 1, further comprising:
receiving, by the computer, an indication from a user that the first and second circuit devices of the plurality of circuit devices are to be abutted.

9. The method of claim 1, wherein the first circuit device is a first optical waveguide and the second device is a second optical waveguide, and wherein the abutting of the first and second optical waveguide forms a combined and continuous optical waveguide.

10. The method of claim 1, further comprising:
rendering, by the computer, the first and second circuit devices including the respective set of pin figures on a graphical user interface (GUI); and
updating, by the computer, the GUI based on abutting the first and second circuit devices.

11. A system for abutting circuit devices in an integrated circuit design, the system comprising:
one or more computers comprising a non-transitory machine-readable media configured to store a plurality of database records of a plurality of circuit devices, wherein a first circuit device of the plurality of circuit devices includes a first set of pin figures and a second circuit device of the plurality of circuit devices includes a second set of pin figures;
at least one computer of the one or more computers, the at least one computer coupled to the non-transitory machine readable media storing the plurality of database records and comprising a processor configured to:
determine that a first pin figure of the first set of pin figures is to be overlapped with a second pin figure of the second set of pin figures based upon the location data of the first circuit device and the second circuit device in the respective database records;
identify a first center location of the first pin figure and a second center location of the second pin figure based on the location data of the first circuit device and the second circuit device in the respective database records;
position at least one of the first circuit and second circuit devices such that the first center location and the second center location overlap;
generate a third circuit device formed by abutting first and second circuit devices and having a portion formed by merging and optimizing the overlapping first and second pin figures; and
update the respective database records of the first and second circuit devices based on the generating of the third circuit device formed by abutting first and second circuit devices, whereby the at least one computer provides a computationally efficient and a flexible centering of the first and second pin figures.

12. The system of claim 11, wherein at least one of the first and second circuit devices is represented by a pcell instance.

13. The system of claim 11, wherein at least one of the first and second circuit devices is represented by a first fixed cell instance.

14. The system of claim 11, wherein at least one of the first and second circuit devices is a transistor.

15. The system of claim 11, wherein at least one of the first and second circuit devices is an optical waveguide or a radio frequency (RF) transmission line.

16. The system of claim 11, wherein the processor is further configured to:
determine that the first pin figure of the first set of pin figures is to be overlapped with the second pin figure of the second set of pin figures based upon rectilinear access directions of the first and second pin figures.

17. The system of claim 11, wherein the processor is further configured to:
automatically identify that the first and second circuit devices from the plurality of circuit devices are to be abutted based on the proximity of the first and second devices determined based on location data of the first and second circuit devices in the respective database records.

18. The system of claim 11, wherein the processor is further configured to:
receive an indication from a user that the first and second circuit devices of the plurality of circuit devices are to be abutted.

19. The system of claim 11, wherein the first circuit device is a first optical waveguide and the second device is a second optical waveguide, and wherein the abutting of the first and second optical waveguide forms a combined and continuous optical waveguide.

20. The system of claim 11, wherein the processor is further configured to:
- render the first and second circuit devices including the respective set of pin figures on a graphical user interface (GUI); and
- update the GUI based on abutting the first and second circuit devices.

* * * * *